United States Patent [19]

Martin

[11] Patent Number: 5,250,680

[45] Date of Patent: Oct. 5, 1993

[54] HETEROGENEOUS SYNTHESIS OF AZEPINONES FROM ESTERS

[75] Inventor: Daniel E. Martin, Lee's Summit, Mo.

[73] Assignee: Merrell Dow Pharmaceuticals Inc., Cincinnati, Ohio

[21] Appl. No.: 939,536

[22] Filed: Sep. 2, 1992

Related U.S. Application Data

[63] Continuation of Ser. No. 673,043, Mar. 21, 1991, abandoned, which is a continuation of Ser. No. 400,658, Aug. 31, 1989, abandoned.

[51] Int. Cl.$^5$ .......................................... C07D 281/02
[52] U.S. Cl. .................................. 540/491; 540/490
[58] Field of Search .................................. 540/490, 491

[56] References Cited

U.S. PATENT DOCUMENTS

| 3,112,554 | 2/1964 | Poos et al. | 540/490 |
| 3,562,257 | 2/1971 | Kugita et al. | 540/491 |
| 3,862,955 | 1/1975 | Grivas | 544/331 |
| 4,552,695 | 11/1985 | Igarashi et al. | 540/491 |
| 4,567,175 | 1/1986 | Takeda et al. | 514/211 |
| 4,805,580 | 2/1989 | Mohacsi et al. | 514/211 |

FOREIGN PATENT DOCUMENTS

0343474 11/1989 European Pat. Off.

OTHER PUBLICATIONS

Akelah "Application of Functionalized polymeric ..." Chem. Rev. 81 557–587 (1981).
Kugita et al. "Synthesis of 1,5-Benzpthiazepine" Chem. Pharm. Bull 18(10) 2028–2073 (1970).
Mary Friser "Reagents for Organic Synthesis" Wiley & Sons vol. 10, pp. 512–518 (1981).
Morrison and Boyd, "Organic Chemistry, 3rd Edition," Allyn and Bacon, Inc., Boston (1973), pp. 1002–1004.
Khym, "Analytical Ion-Exchange Procedures in Chemistry and Biology, Theory, Equipment, Techniques," Prenice-Hall, Inc., Englewood Cliffs, N.J. (1974), pp. 15 & 62–65.
Ricci et al. "Similarity of the oxidation . . . " J. Biol. Chem. 258 (17) 10511–10517 (1983).
Kugita et al., A Mild and Selective Method of Ester Hydrolysis, Synth. Commun., 19 (3 & 4), pp. 627–631 (1989).
Kohler et al., J. Am. Chem. Soc., 49, pp. 3181–3188 (1927), "An Apparatus for Determining both the Quantity of Gas Evolved and the Amount of Reagent Consumed in Reactions with Methyl Magnesium Iodide".

Primary Examiner—Alan L. Rotman
Assistant Examiner—Celia Chang
Attorney, Agent, or Firm—Neal O. Willmann

[57] ABSTRACT

An amino-acid ester compound can be cyclized into a cyclic amido-carbonyl compound by contacting the amino-acid ester compound in a liquid medium with a heterogeneous acidic ion-exchange substance. For example, 2-hydroxy-3-(2-aminophenylthio)-3-(4-methoxyphenyl)propionic acid, methyl ester, threo form, can be cyclized in an aqueous mixture into cis-2-(4-methoxyphenyl)-3-hydroxy-2,3-dihydro-1,5-benzothiazepin-4(5H)-one by employing a sulfonated polystyrene-divinylbenzene ion-exchange resin in its acid form, e.g., Dowex® 50X4-400. at yields exceeding 85 percent of theory, and the product can be used to make diltiazem hydrochloride.

1 Claim, No Drawings

HETEROGENEOUS SYNTHESIS OF AZEPINONES FROM ESTERS

This is a continuation of application Ser. No. 07/673,043, filed Mar. 21, 1991 now abandoned which is a continuation in part of application Ser. No. 07/400,658, filed Aug. 31, 1989, now abandoned.

FIELD

This invention concerns organic cyclization reactions employing ion-exchange substances, useful for preparing organic compounds, e.g., benzothiazepine pharmaceuticals.

BACKGROUND

Kugita et. al., U.S. Pat. No. 3,562,257 (Feb. 9, 1971), discloses benzothiazepine derivatives, among which is (+)-cis-5-[2-(dimethylamino)ethyl]-2,3-dihydro-3-hydroxy-2-(4-methoxyphenyl)-1,5-benzothiazepin-4(5H)-one acetate (ester) hydrochloride, i.e., diltiazem hydrochloride Diltiazem hydrochloride is a well-known coronary vasodilator.

The current, known commercial process for preparing diltiazem hydrochloride involves the following two steps: (1) hydrolysis of an ester, e.g., the methyl ester, to form the corresponding free propionic acid, and then (2) heating of the free propionic acid in xylenes to cyclize it into 1,5-benzothiazepine, which is further processed into diltiazem and then its hydrochloride. See generally, Igarashi et. al., U.S. Pat. No. 4,552,695 (Nov. 12, 1985), e.g., at column 7, lines 10-47.

Known prior art has shown attempts to cyclize the ester, e.g., the methyl ester, directly into the 3-(hydroxy)-2,3-dihydro-2-(4-methoxyphenyl)-1,5-benzothiazepine. Also, direct cyclization attempts have been generally disclosed in the preparation of an 8-chloro analog of diltiazem. However, yields are generally low.

For example, Kugita et. al., Chem. Pharm. Bull., 18(10), 2028-2037 (1970), reports on synthesis of 1,5-benzothiazepine derivatives, to include at page 2032 thereof, where it is reported that cyclization of the amino ester into the 1,5-benzothiazepine was effected by heating the ester with sulfuric acid or with acetic acid, but that hydrolysis of the amino ester to the amino carboxylic acid and cyclization of the amino acid in boiling xylene gave more satisfactory yield of the cyclic amide.

And, Takeda et. al., U.S. Pat. No. 4,567,175 (Jan. 28, 1986), discloses 8-chloro-1,5-benzothiazepine derivatives, to include cyclization attempts of esters such as is illustrated at columns 5-7 and described at column 7, lines 54-56, and at from column 8, line 65, to column 9, line 8. Cyclizations of the acid compounds are also illustrated and described therein.

Basu et. al., Synth. Commun., 19(3 & 4), 627-631 (1989), reports on a mild and selective method of ester hydrolysis. This method employs Dowex-50 resin.

What is lacking and needed in the art is a more efficient way to prepare such a benzothiazepine as diltiazem hydrochloride, and so forth, particularly on a commercial scale. Desirably, any solution to such a problem perhaps would also be able to be applied in preparations of other organic compounds, and other problems also might be solved as well.

SUMMARY

This invention provides a procedure for cyclization of an amino-acid ester compound comprising contacting the amino-acid ester compound in a liquid medium with a heterogeneous acidic ion-exchange substance under conditions sufficient to form a cyclic amido-carbonyl compound.

The present invention is useful for preparing cyclic organic compounds, especially to include such compounds as 1,5-benzothiazepines. In particular, 1,5-benzothiazepines as the well-known diltiazem and diltiazem hydrochloride and so forth can be so prepared.

Embodiments of this invention particularly are characterizable in being highly efficient. In fact, they may be considered to be unexpectedly efficient in the yields which can be obtained thereby and surprisingly well-adapted to commercial production. Yields can be high and may be considered to be surprisingly so. Moreover, the invention can provide a breakthrough in the art by reducing the number of synthetic steps heretofore required in the known commercial production of such a pharmaceutical as diltiazem hydrochloride while yet providing high yields. Further, the practice of the invention does not generally require expensive reagents or solvents, or chemicals presently known to be highly dangerous in general, and it can be carried out safely in general on an industrial scale. The ion-exchange substance may be regenerated and recycled for further use.

Further advantages attend the invention as well.

ILLUSTRATIVE DETAIL

Herein, a procedure is a method and/or process.

Herein, the term "amino-acid ester compound" refers to an organic chemical compound which contains an amino functionality having at least one active hydrogen atom therein as determined by the Zerewitinoff test, see generally, Kohler et. al., *J. Am. Chem. Soc.*, 49, 3181-3188 (1927), and which contains an organic ester functionality of an acid. The amino-acid ester compound is generally such that it will generally cyclize, preferably internally, during the procedure of the invention. Desirably, the amino functionality has two active hydrogen atoms therein as determined by the Zerewitinoff test; the ester functionality is an ester of a carboxylic acid, and the amino functionality and the carbonyl carbon of the carboxylic acid ester are separated by from three to six other atoms as in a backbone of the compound. The ester is advantageously an alkyl ester, especially a lower alkyl ester, to include, of course, propyl, ethyl and methyl esters. The methyl ester is the preferred ester in carrying out the practice of the present invention.

Preferably, the amino-acid ester compound employed in the practice of this invention is represented by compound of the following general formula:

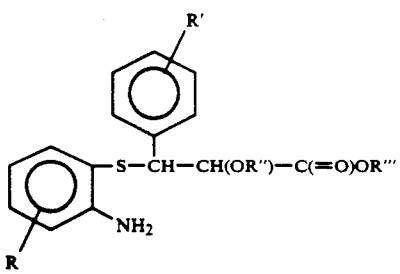

(I)

wherein
R is a generally inert moiety;
R' is a generally inert moiety;
R" is a generally inert moiety, and
R'" is alkyl.

The term "generally inert" refers herein to hydrogen and other moieties which do not generally interfere with the procedural practice of this invention. Representative examples of generally inert groups or moieties may generally include such organic groups as, for instance, aromatics to include phenyl, alkyl- and/or halogen-substituted phenyl, naphthyl, phenyl-, alkyl- and/or halogen-substituted naphthyl, fused-ring aromatics to include fused-ring phenyl, fused-ring alkyl- and/or halogen-substituted phenyl, fused-ring naphthyl, fused-ring phenyl-, alkyl- and/or halogen-substituted naphthyl, and so forth, saturated organics to include alkyl, which includes cycloalkyl, for example, methyl, ethyl, propyl to include cyclopropyl, butyl to include cyclobutyl and methyl-substituted cyclopropyl, pentyl to include, e.g., cyclopentyl and methyl-substituted cyclobutyl, hexyl to include, e.g., cyclohexyl, methylsubstituted cyclopentyl and di-methyl or ethyl-substituted cyclobutyl, heptyl to include cycloheptyl, etc., octyl to include cyclooctyl, etc., halogen-substituted alkyl to include halogen-substituted cycloalkyl, e.g., fluoroalkyl, perfluoroalkyl, e.g., trifluoromethyl, and chloralkyl, alkoxy, e.g., methoxy, aromatic-oxy, e.g., phenoxy, alkthioxy, e.g., methylthioxy, aromatic-thioxy, e.g., phenylthioxy, acyl, e.g., benzoyl and acetyl, and so forth and the like. Representative examples of generally inert groups which may more appropriately reside on an aromatic ring, to include as being R or R', may generally further include lower alkoxy, e.g., methoxy, halogens, e.g., fluoro, chloro, and bromo, lower acyl, e.g., acetyl, lower alkyl, e.g., methyl, trifluoromethyl, nitro, and so forth and the like.

Of the compounds represented by the formula (I), the following are especially noted as being those wherein R is H, or Cl, to include those having the Cl para to the required amino moiety of the aromatic ring, but preferably H;

R' is para-positioned, and/or lower alkoxy, H, lower acyl, lower alkyl, trifluoromethyl, or nitro, but preferably para-methoxy;

R" is H or lower acyl, especially acetyl, but preferably H, and

R'" is lower alkyl, but preferably methyl.

Also of note, the amino-acid ester sample employed may be optically inactive or optically active, and the procedure of the invention can be employed with all types of isomers to include, for example, threo and erythro amino-acid esters of the formula (I), which cyclize to form cis and trans cyclic amido-carbonyl compounds of the formula (II), respectively. It may well be advantageous to employ an appropriate optically enriched or optically pure amino-acid ester sample in the practice of the present invention, especially in procedures which lead up to cyclic amidocarbonyl compounds which are employed as intermediates to make optically active final products. Such is the case with diltiazem hydrochloride for one illustration of note.

Of particular note, the amino-acid ester sample employed should be of a suitable purity in the practice of this invention. If the amino-acid ester sample is not of a suitable purity, the procedure of this invention may result in undesirably low, or possibly no appreciable, yields.

Herein, the term "liquid medium" refers to a substance which is substantially liquid during the procedure of the invention. Typically, the liquid medium functions at a minimum as diluent in the practice of this invention. The liquid medium employed in cyclization in this invention is generally a hydroxylated compound such as in water and alcohols, with an aqueous diluent being preferred at that stage. More than one substance or diluent may be employed, as appropriate.

Herein, the term "heterogeneous acidic ion-exchange substance" refers to a substance which is generally considered a solid and which has acid functionality suitable for carrying out the practice of this invention bonded therewith. Thus, the heterogeneous acidic ion-exchange substance can be of synthetic polymer matrix, i.e., resin, with appropriate acidic functionalities bonded thereto, and may also include other types of exchange substances typically of high capacity acidic functionality such as appropriate inorganic ion-exchange crystals and exchange materials made by introducing appropriate acidic functional groups into polyacrylamide gels, celluloses, or dextrans, and so forth and the like. Preferably however, the heterogeneous acidic ion-exchange substance is an acidic ion-exchange resin, especially of the strong acid type, to include a strong acid phenolic type such as, for example, a sulfonated phenolic type ion-exchange resin in its acid form, e.g., Bio Res ® 40, etc., but particularly one such as, for example, a so-called sulfonated polystyrene-type ion-exchange resin, to include a polystyrene-divinylbenzene ion-exchange resin, in its acid form. Examples of commercially available sulfonated polystyrene-divinylbenzene ion-exchange resins include Amerlite ® IR-120, Dowex ®-50, Duolite (TM) C-20, Ionac ® GCG-240, Lewatit (TM) S-100, Permutit ® Q, Rexyn ® 101 and Zeocarb (TM) 225.

The heterogeneous acidic ion-exchange substance can be embodied in many forms. Beads are one example of this. Also, it can be advantageous to embody the heterogeneous acidic ion-exchange substance in a form such as a coating over a substantial area of a reaction vessel or chamber, or as a large plate or plates therein. Such embodiments as these more substantial latter-mentioned forms can provide, for example, a macro-solid form, from which cyclized organic compound may precipitate, and which thus can be used to advantage in separation of such precipitates from the remainder of any liquid reaction system found in the practice of this invention.

Herein, the term "cyclic amido-carbonyl compound" refers to an organic compound which is heterocyclic, as a minimum, generally due to an amido nitrogen, formerly of the aminoacid ester compound, being coupled to a carbonyl carbon, also formerly of the amino-acid ester compound, therein. Preferably, this required heterocyclic feature of the cyclic amido-carbonyl compound is embodied in a five to eight atom ring. It is especially preferred to have another hetero atom, for example, a sulfur atom, in the formed ring. Desirably, the heterocyclic amido nitrogen bears one active hydrogen as determined by the Zerewitinoff test.

Preferably, the cyclic amido-carbonyl compound is a 1,5-benzothiazepine, and especially a 1,5-benzothiazepine represented by a compound of the following general formula:

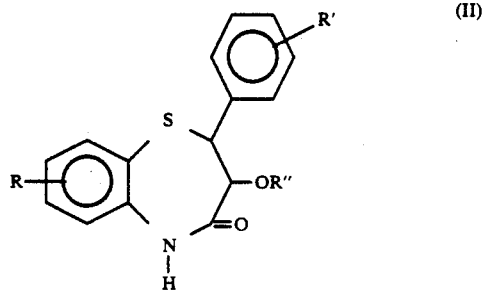

wherein R, R' & R" are as defined in the formula (I).

Especially noted cyclic amido-carbonyl compounds thus particularly include those of the formula (II) wherein R is H or 8-chloro, but preferably H;

R' is para-positioned, and/or lower alkoxy, H, lower acyl, lower alkyl, trifluoromethyl, or nitro, but preferably para-methoxy, and R" is H In the practice of this invention, the amino-acid ester compound is contacted in the liquid medium with the heterogeneous acidic ion-exchange substance. In general, cyclization of the amino-acid ester compound takes place. The procedure of the present invention is carried out under conditions which are sufficient to prepare the cyclic amidocarbonyl compound.

The procedure of this invention is a heterogeneous phase procedure. It employs the generally solid heterogeneous acidic ion-exchange substance in the liquid medium to prepare the cyclic amido-carbonyl compound.

Generally speaking, although the liquid medium may itself be composed of, say, the amino-acid ester compound, i.e., the reaction may be run essentially neat with respect to the amino-acid ester compound, the liquid medium is typically provided by a substance other than the amino-acid ester compound itself and which is substantially liquid during the procedure of the invention. Water is the preferred liquid medium.

The procedure of the present invention can be carried out under batch-type processing conditions. Flow-type processing conditions can be employed as appropriate by those of skill in the art as well.

Concentrations of the amino-acid ester compound in relation to the liquid medium employed can vary widely. However, initial concentrations of the amino-acid ester compound in the liquid medium, especially in relation to batch-type processing, more typically reside within concentrations about from 0.01 molar (M) to saturation levels, or even higher such as found in slurries, to generally include concentrations about from 0.05 to 1 M and about from 0.1 to 0.6 M. Preferably however, the amino-acid ester compound is essentially dissolved into the liquid medium in the practice of this invention.

Amounts of the heterogeneous acidic ion-exchange substance which are employed in the practice of this invention are in general any which effect preparation of the cyclic amido-carbonyl compound. A suitable amount of acid functionality will thus reside on the ion-exchange substance employed.

Temperatures employed in carrying out the procedure of the present invention are generally any which suffice to prepare the cyclic amido-carbonyl compound. However, temperatures about from 50 to 150 degrees C. are more typically employed, to generally include those about from 80 to 120 degrees C. Reflux conditions can advantageously be employed, particularly when employing aqueous liquid media. Notably, the temperatures employed in carrying out the procedure of this invention thus can be fairly moderate.

Agitation of the amino-acid ester compound in the liquid medium is typically employed. This helps bring about more efficient contact in the practice of the invention.

Duration of the contact or the time required to bring about the preparation of the cyclic amido-carbonyl compound is generally that time required which brings about the desired level of completion in the procedure of the invention. In batch-type processing, such a time includes times about from several minutes to several days or more. More typically, the time employed in the practice of this invention ranges about from an hour or two to two or so days.

Prepared cyclic amido-carbonyl compound may be employed in further processing such as in reactions as a chemical intermediate without its separation from the remaining components employed to make it, or it may be collected and separated from the remaining components employed to make it, as desired. Known methods can be employed.

For example, the prepared cyclic amido-carbonyl compound can be generally insoluble in the liquid medium employed. In this case, the cyclic amido-carbonyl compound can be collected directly by scooping, decanting, straining or filtering, which can be particularly advantageous when the acidic ion-exchange resin is embodied as the more substantially-sized forms such as described before. Alternatively, the cyclic amido-carbonyl compound can be extracted from the liquid medium employed by using a suitable extraction solvent, and then it can be recovered from the extractant solution by evaporation, crystallization techniques or chromatographic methods, et cetera, if so desired.

The heterogeneous acidic ion-exchange substance is typically used in its acidic, i.e., hydrogen ion, form. Generally, the ion-exchange substance may be regenerated and recycled for further use.

Yields of the cyclic amido-carbonyl compound can be high. Preferred practice within the spirit of this invention can provide yields of the cyclic amido-carbonyl compound as great as at least about 50 percent of theory, at least as great as about 60 percent of theory, at least as great as about 70 percent of theory, and at least as great as about 80 percent of theory to include at least as great as about 85 percent of theory.

Purity of the product can be from good to excellent. The cyclic amido-carbonyl compound prepared by the practice of this invention can have a high enough quality purity that the compound can be employed in its freshly prepared state as a reactant in further derivitizations. For example, (+)-(2S,3S)-cis-2-(4-methoxyphenyl)-3-hydroxy-2,3-dihydro-1,5-benzothiazepin-4(5H)-one prepared by the practice of the present invention can be immediately employed to make diltiazem hydrochloride by known N-alkylation, acylation and acid salt formation steps. Other derivatives can be analogously prepared. Of course if desired, the cyclic amido-carbonyl compound can be itself further purified, to render it to be a very high or even ultra high purity compound, such as can be carried out by recrystallization techniques, chromatographic methods, and so forth.

The following examples further illustrate the invention. Therein, parts and percentages are by weight unless otherwise specified.

Example 1

Cyclization of racemic 2-hydroxy-3-(2-aminophenylthio)-3-(4-methoxyphenyl)propionic acid, methyl ester, threo form, into racemic cis-2-(4-methoxyphenyl)-3-hydroxy-2,3-dihydro-1,5-benzothiazepin-4(5H)-one was carried out as follows:

Into a 50-mL round-bottom flask fitted with a magnetic stirrer, reflux condenser, and nitrogen adapter, was added a sample of racemic 2-hydroxy-3-(2-aminophenylthio)-3-(4-methoxyphenyl)propionic acid, methyl ester, threo form (2.50 g, 0.00750 mol). To this was added 0.768 g of moist Dowex ® 50X4-400 ion-exchange resin, which previous to this had been soaked in 4 N HCl overnight and then washed with deionized water until the washings gave a neutral pH. Next was added 23 mL of water. The reaction vessel was lowered into an oil bath at about 120 degrees C., and the mixture therein was stirred. At about 18¼ hours after the heating and stirring began, thin layer chromatography (TLC) analysis (1:1 hexane, ethyl acetate) indicated that the desired thiazepine product was then forming, and a spot at the origin of the TLC plate was also present.

At about 50 minutes thereafter, an additional 0.756 g of moist Dowex ® 50X4-400 in its acid form plus 10 mL of water were added to the mixture, and the oil bath was adjusted to about 115 degrees C. At about 4¼ hours after these additions and this adjustment to the oil bath, TLC still indicated the spot at the origin, and the mixture was allowed to continue stirring and heating for about 15¼ hours further, whereupon TLC indicated a very faint spot at the origin with the only other spot appearing to be from the desired thiazepine product.

About one-half of an hour later the heating was stopped, and the mixture was cooled slightly and filtered by fast filtration with the mixture yet warm. Solids which were collected were washed well with room temperature water. The collected, damp solids were slurried in 50 mL of acetone, and heating of the slurry below reflux dissolved solid product. The hot acetone mixture was filtered to collect the insoluble Dowex ® resin on filter paper. The Dowex ® resin was dried to yield 0.70 g. The acetone filtrate was evaporated to dryness to obtain the desired product as a white solid (1.96 g, 86.7 percent yield of theory), confirmed by proton nuclear magnetic resonance (HNMR) spectroscopy, TLC analysis in comparison to a reference standard, and mass spectroscopy.

Example

Cyclization of racemic 2-hydroxy-3-(2-aminophenylthio)-3-(4-methoxyphenyl)propionic acid, methyl ester, threo forms, into racemic cis-2-(4-methoxyphenyl)-3-hydroxy-2,3-dihydro-1,5-benzothiazepin-4(5H)-one was carried out as follows:

Into a 100-mL round-bottom flask fitted with a magnetic stirrer, reflux condenser, and nitrogen adapter, was added a sample of racemic 2-hydroxy-3-(2-aminophenylthio)-3-(4-methoxyphenyl)propionic acid, methyl ester, threo form (2.50 g, 0.00750 mol). To this was added 1.52 g of moist Dowex ® 50X4-400 ion-exchange resin, which previous to this had been soaked in 4 N HCl overnight and then washed with deionized water until the washings gave a neutral pH. Next was added 33 mL of water. The reaction vessel was lowered into an oil bath at about 117 degrees C., and the mixture therein was stirred. At about 16¼ hours after the heating and stirring began, TLC analysis (1:1 hexane, ethyl acetate) indicated that the desired thiazepine product had formed, and a faint spot at the origin of the TLC plate was also present.

About one-half of an hour later the heating was stopped, and the mixture was cooled somewhat and filtered to collect solids. The solids which were collected were washed well with room temperature water. The collected, damp solids were slurried in 35 mL of acetone, and the acetone slurry was heated to boiling. The hot acetone mixture was filtered to collect the insoluble Dowex ® resin, which was rinsed with two 25-mL portions of room temperature acetone followed by a 40-mL portion of hot acetone. The Dowex ® resin was dried to yield 0.75 g. The acetone filtrate was combined with the acetone rinsings, and this was evaporated to dryness to obtain the desired product as a slightly off-white white solid (1.91 g, 84.5 percent yield of theory), confirmed by HNMR spectroscopy as consistent with the proposed product structure and appearing to be fairly clean of extra signals, and by TLC analysis in comparison to a reference standard.

Example 3

Cyclization of racemic 2-hydroxy-3-(2-aminophenylthio)-3-(4-methoxyphenyl)propionic acid, methyl ester, threo form, into racemic cis-2-(4-methoxyphenyl)-3-hydroxy-2,3-dihydro-1,5-benzothiazepin-4(5H)-one was carried out as follows:

The procedure of Example 2 was repeated, except that 1.52 g of moist Amberlite ® IR-120 (plus) ion-exchange resin, which previously had been soaked in 4 N HCl overnight and then washed with deionized water until the washings gave a neutral pH, was used in place of the Dowex ® 50X4-400.

Also, at about 16¼ hours after heating and stirring began, the heating was stopped, and the mixture was cooled slightly and filtered to collect solids. The solids which were collected were slurried in 45 mL of acetone, and the acetone slurry was warmed slightly. The warm acetone mixture was filtered to collect the insoluble Amberlite ® resin, which was rinsed with a 75-mL portion of room temperature acetone. The Amberlite ® resin was dried to yield 1.293 g. The acetone filtrate was combined with the acetone rinsing, and this was evaporated to dryness to obtain the desired product as a white solid (1.61 g, 71.2 percent yield of theory), confirmed by TLC analysis in comparison to a reference standard.

Example 4

Cyclization of (+)-(2S,3S)-2-hydroxy-3-(2-aminophenylthio)-3-(4-methoxyphenyl)propionic acid, methyl ester, threo form, into (+)-(2S,3S)-cis-2-(4- methoxyphenyl)-3-hydroxy-2,3-dihydro-1,5-benzothiazepin-4(5H)-one was carried out as follows:

Into a 50-mL round-bottom flash fitted with a magnetic stirrer, reflux condenser, and nitrogen adapter, was added a sample of (+)-(2S,3S)-2-hydroxy-3-(2-aminophenylthio)-3-(4-methoxyphenyl)propionic acid, methyl ester, threo form, having a specific rotation at 24 degrees C. at 578 nm of+ 309 degrees (0.0508 g in 10 mL methanol) (1.50 g, 0.00450 mol). To this was added 0.92 g in 10 mL methanol) 1.50 g, 0.00450 exchange resin, which previous to this had been soaked in 4 N HCl overnight and then washed with deionized water until the washings gave a neutral pH. Next was added 20 mL of water. The reaction vessel was lowered into an oil bath at about 119 degrees C., and the mixture therein was stirred. At about 17½ hours after the reaction vessel was lowered into the oil bath and stirring began, heating and stirring were discontinued automatically.

At about 4½ hours after the heating and stirring was stopped, the room temperature mixture was filtered to collect solids. The solids which were collected were washed with deionized water. The collected, damp solids were slurried in 30 mL of acetone, and the acetone slurry was heated to near boiling. The hot acetone mixture was filtered to collect the insoluble Dowex ® resin, which was rinsed with a 45-mL portion of room temperature acetone. The Dowex ® resin was dried to yield 0.430 g. The acetone filtrate was combined with the acetone rinsing, and this mixture was evaporated to dryness to obtain the desired product as a white solid (1.20 g, 88.9 percent yield of theory), confirmed by HNMR spectroscopy as consistent with the proposed product structure, appearing to be very clean of extra signals, and by TLC analysis (1:1 hexane, ethyl acetate) in comparison to a reference standard. It had a melting point of 202–203 degrees C., a specific rotation at 24 degrees C. at 578 nm of+121 degrees (0.0522 g in 10 mL ethanol) and a specific rotation at 24 degrees C. at 589 nm of+114 degrees (0.0522 g in 10mL ethanol).

Example 5

Cyclization of pure 2-hydroxy-3-(2-amino-5-chlorophenylthio)-3-(4-methoxyphenyl)propionic acid, methyl ester, threo form, into cis-2-(4-methoxyphenyl)-3-hydroxy-2,3-dihydro-8-chloro-1,5-benzothiazepin-4(5H)-one is generally carried out by such procedures as described in the preceding examples.

Example 6

The products of Examples 1–4 are separately used to make "racemic" or optically active diltiazem hydrochloride. The product of Example 5 is used to make cis-2-(4-methoxy-phenyl)-3-acetoxy-2,3-dihydro-5-[2-(dimethylamino)ethyl]-8-chlor-1,5-benzothiazepin-4(5H)-one, maleate salt. N-Alkylation, acetylation, and acid salt formation steps are employed, and the yields are generally excellent.

CONCLUSION

The present invention is thus provided. Numerous adaptations and modifications can be effected by those skilled in the art within the spirit of this invention, the scope of which is particularly pointed out by the following distinctly claimed subject matter.

What is claimed is:

1. A procedure for cyclization of an amino-acid ester compound comprising contacting the amino-acid ester compound in an aqueous medium with a heterogeneous acidic ion-exchange resin under conditions sufficient to form a cyclic amido-carbonyl compound, said amino-acid ester compound being represented by a compound of the following formula:

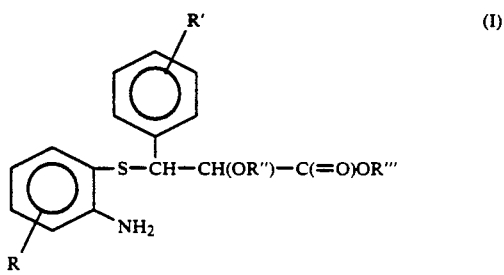

wherein
R is H or Cl;
R' is selected from the group consisting of H, lower alkoxy, lower alkyl, lower acyl, trifluoromethyl and nitro;
R" is H or acetyl; and
R''' is lower alkyl; and
said cyclic amido-carbonyl compound is represented by a compound of the formula:

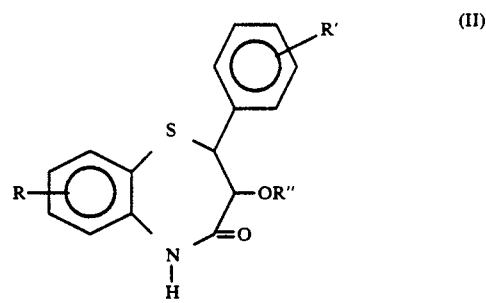

wherein R, R' and R" are as defined in Formula (I).

* * * * *